(12) United States Patent
Kurata

(10) Patent No.: US 7,827,623 B2
(45) Date of Patent: Nov. 9, 2010

(54) WEARING ARTICLE AND METHOD OF MANUFACTURING THE SAME

(75) Inventor: Shuhei Kurata, Settsu (JP)

(73) Assignee: Zuiko Corporation (JP)

( * ) Notice: Subject to any disclaimer, the term of this patent is extended or adjusted under 35 U.S.C. 154(b) by 1064 days.

(21) Appl. No.: 10/541,089

(22) PCT Filed: Jan. 9, 2004

(86) PCT No.: PCT/JP2004/000112

§ 371 (c)(1),
(2), (4) Date: Jun. 29, 2005

(87) PCT Pub. No.: WO2004/062398

PCT Pub. Date: Jul. 29, 2004

(65) Prior Publication Data

US 2006/0174400 A1     Aug. 10, 2006

(30) Foreign Application Priority Data

Jan. 10, 2003    (JP) .............................. 2003-004905
Apr. 30, 2003    (JP) .............................. 2003-124802

(51) Int. Cl.
*A41B 9/00* (2006.01)
(52) U.S. Cl. ................................. 2/400; 2/69
(58) Field of Classification Search ....... 2/400, 2/406; 156/84, 73.3; 60/372, 389, 369, 385.12, 60/385.23, 385.24, 385.26
See application file for complete search history.

(56) References Cited

U.S. PATENT DOCUMENTS

| | | | | |
|---|---|---|---|---|
| 1,577,409 A | * | 3/1926 | Rand | 2/401 |
| 2,408,723 A | * | 10/1946 | Arpin et al. | 2/403 |
| 2,462,195 A | * | 2/1949 | Jacobson | 2/406 |
| 2,663,022 A | * | 12/1953 | Aaronson | 2/80 |
| 2,771,881 A | * | 11/1956 | Betts | 2/466 |
| 3,819,401 A | * | 6/1974 | Massengale et al. | 156/85 |
| 3,912,565 A | * | 10/1975 | Koch et al. | 156/85 |
| 4,031,568 A | * | 6/1977 | Huff | 2/406 |
| 4,050,462 A | * | 9/1977 | Woon et al. | 604/365 |
| 4,253,461 A | * | 3/1981 | Strickland et al. | 604/389 |
| 4,326,528 A | * | 4/1982 | Ryan et al. | 604/385.26 |

(Continued)

FOREIGN PATENT DOCUMENTS

EP    0 797 970    10/1997

(Continued)

*Primary Examiner*—Katherine Moran
*Assistant Examiner*—Richale L Quinn
(74) *Attorney, Agent, or Firm*—Gerald E. Hespos; Michael J. Porco

(57) ABSTRACT

A wearing article (4 to 4D) includes a main body (5 to 5D) having a front part (P), a back part (Q) and a crotch part (R) coupling the front part (P) and the back part (Q). The main body (5A to 5D) includes a pair of waist edges (T) opposed to each other and a pair of leg edges (S) opposed to each other. A shirring (15) is so formed in a substantially widthwise middle portion of the crotch part (R) of the main body (5 to 5D) as to shorten a space between the front part (P) and the back part (Q). A ratio of the length (L1) of the crotch part (R) along the forward and backward direction (X) to a length (L2) between the pair of waist edges (T) is 1:15 to 1:2.

18 Claims, 14 Drawing Sheets

U.S. PATENT DOCUMENTS

| | | | |
|---|---|---|---|
| 4,381,781 A * | 5/1983 | Sciaraffa et al. | 604/372 |
| 4,464,217 A | 8/1984 | Dickover et al. | |
| 4,515,595 A * | 5/1985 | Kievit et al. | 604/385.3 |
| 4,758,241 A * | 7/1988 | Papajohn | 604/387 |
| 4,795,451 A * | 1/1989 | Buckley | 604/385.26 |
| 4,842,596 A * | 6/1989 | Kielpikowski et al. | 604/385.26 |
| 4,857,067 A * | 8/1989 | Wood et al. | 604/389 |
| 4,935,021 A | 6/1990 | Huffman et al. | |
| 5,489,282 A * | 2/1996 | Zehner et al. | 604/385.26 |
| 5,496,429 A * | 3/1996 | Hasse et al. | 156/73.3 |
| 5,576,091 A | 11/1996 | Zajaczkowski et al. | |
| 5,858,151 A | 1/1999 | Igaue et al. | |
| 6,049,916 A | 4/2000 | Rajala et al. | |
| 6,240,569 B1 | 6/2001 | Van Gompel et al. | |
| 6,648,865 B1 * | 11/2003 | Stiehl et al. | 604/385.01 |
| 6,703,537 B1 * | 3/2004 | Roe et al. | 604/369 |
| 2005/0177126 A1 * | 8/2005 | Kurata | 604/387 |
| 2007/0208319 A1 * | 9/2007 | Minato | 604/385.26 |

FOREIGN PATENT DOCUMENTS

| | | |
|---|---|---|
| GB | 741710 | 12/1955 |
| JP | 3101936 | 10/1991 |
| JP | 4-242643 | 8/1992 |
| JP | 7-255778 | 9/1995 |
| JP | 9506004 | 6/1997 |
| JP | 2000-93462 | 4/2000 |
| JP | 2001-224615 | 8/2001 |
| JP | 2002-209942 | 7/2002 |
| JP | 2002-320641 | 11/2002 |
| JP | 2003-19163 | 1/2003 |

* cited by examiner

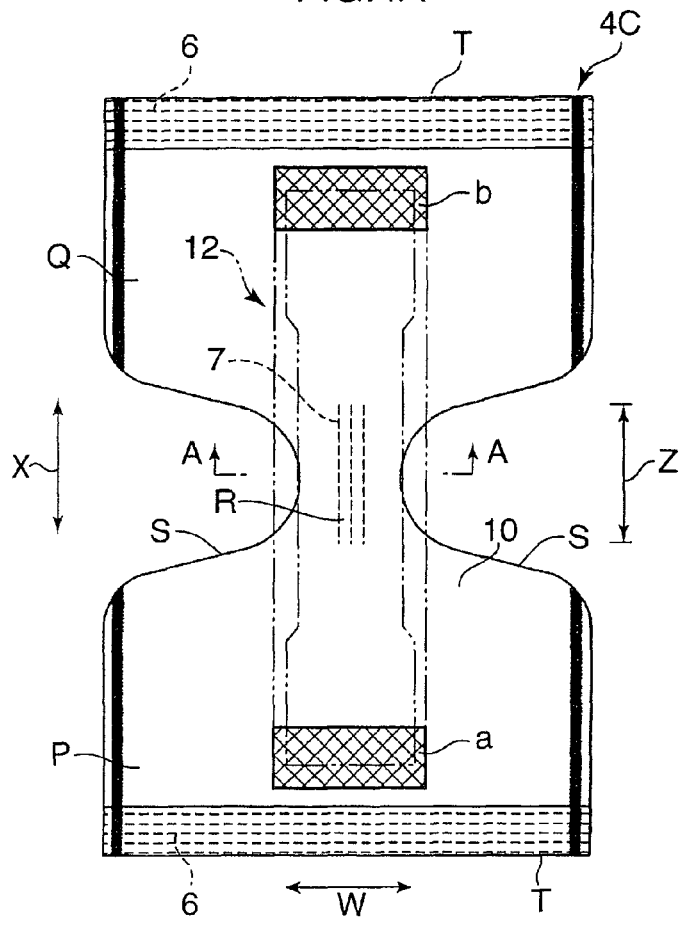
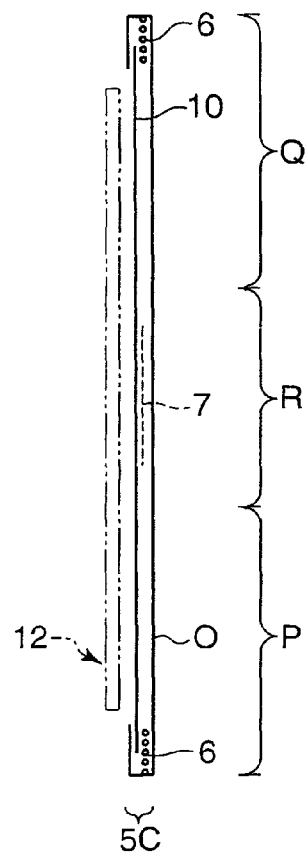
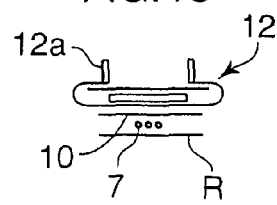

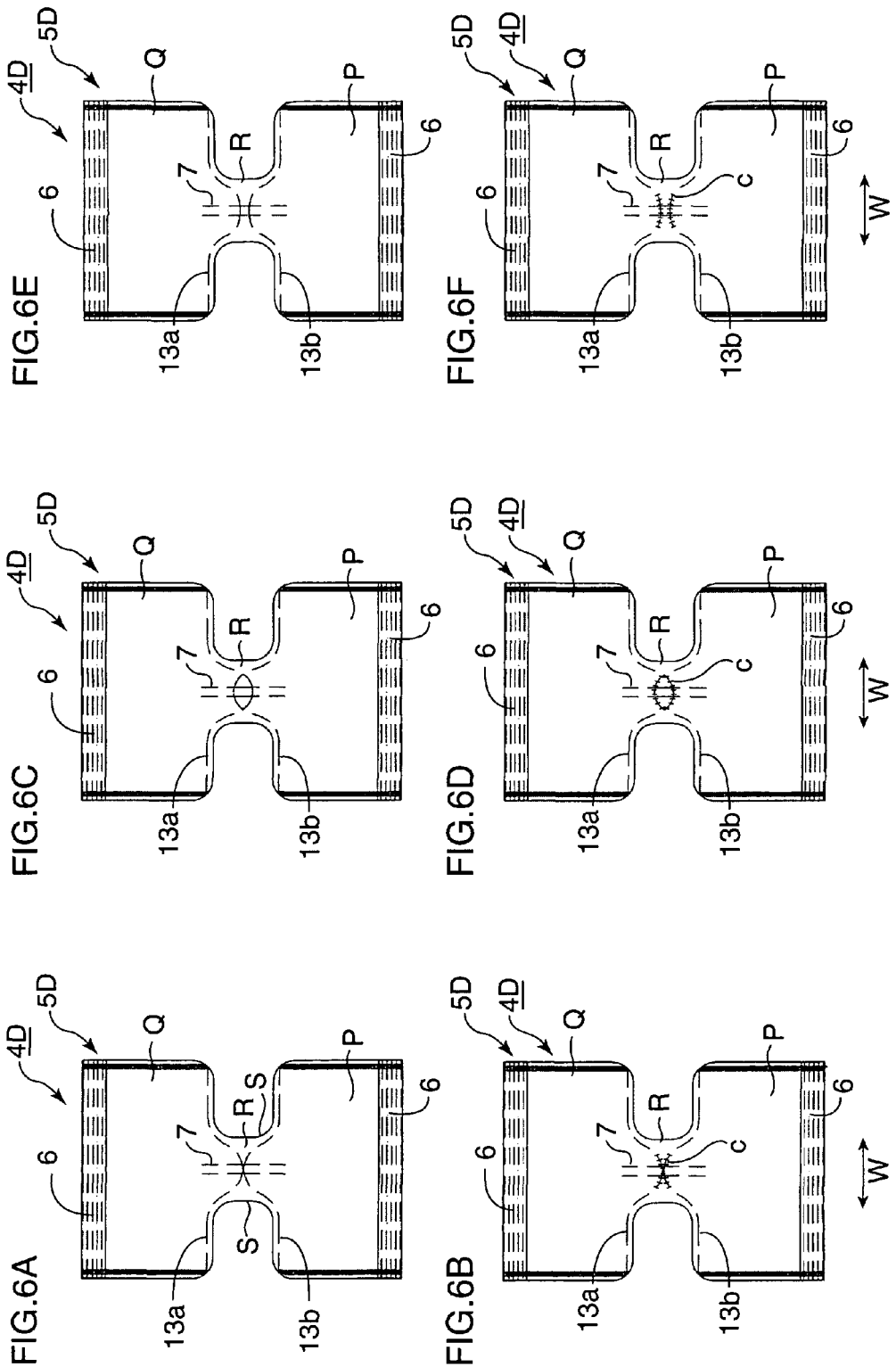

(4)

(5)

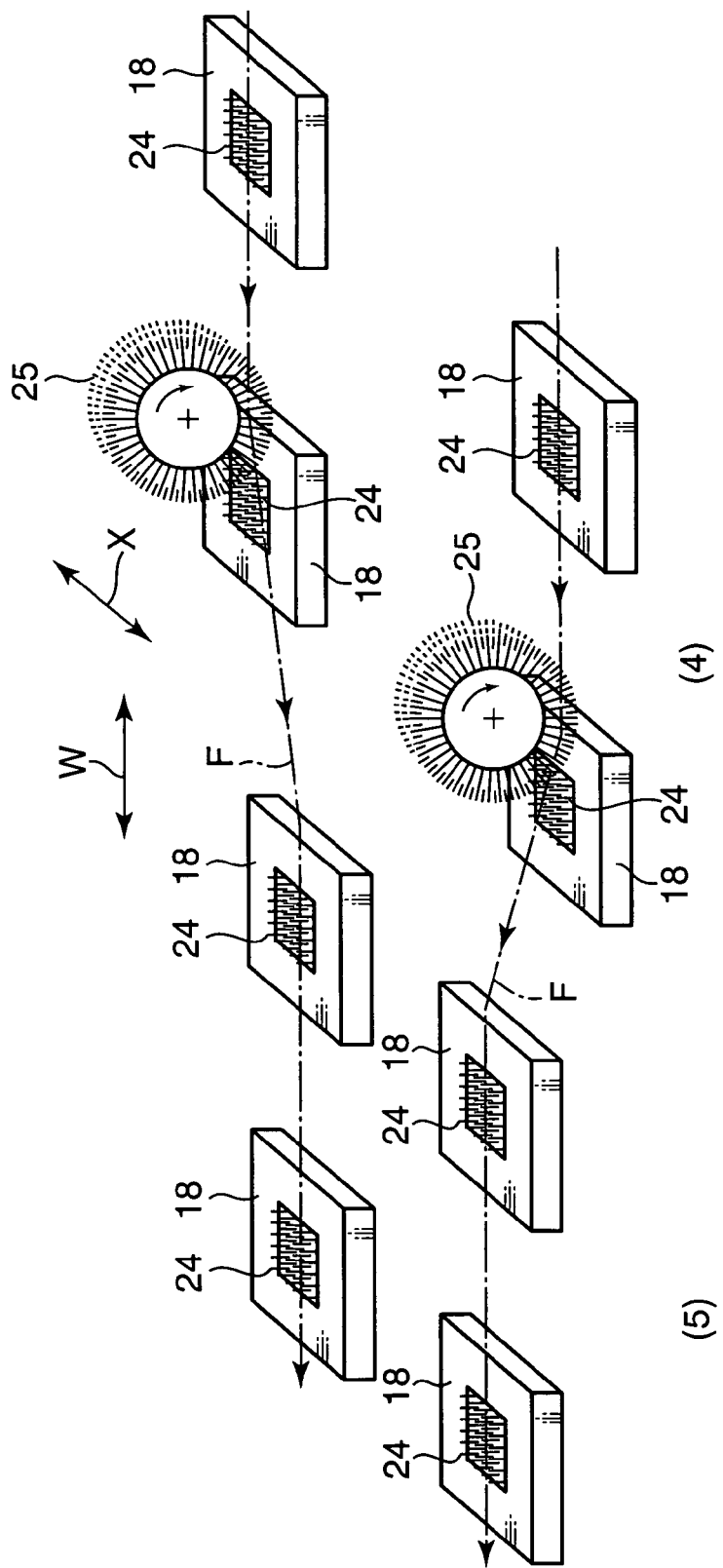

WEARING ARTICLE AND METHOD OF MANUFACTURING THE SAME

TECHNICAL FIELD

The present invention relates to a wearing article having improved wear comfort and a method for producing the same.

BACKGROUND TECHNOLOGY

There have been proposed disposable underpants 1 (wearing article) 1 of the trunks type formed with a body opening 1a and both leg openings 1b and having elastic members 2 for waist attached around the body opening 1a under a stretched state in widthwise direction as shown in FIG. 16 (Japanese Unexamined Patent Publication No. 2001-224615).

If an absorbent is attached to a crotch part 1c of such disposable underpants, the disposable underpants can be used as a pants-type diaper or training parts for infants and small children or incontinence underpants for adults.

There have been also disclosed pants-type fitting articles having an absorbent including elastic members attached to the inner surface thereof (Japanese Unexamined Patent Publications Nos. 2002-209942, 2002-320641, 2003-19163).

There has been also disclosed pants-type absorbent article in which elastic members are arranged at a crotch part and a back part (back body) (Japanese Unexamined Patent Publication No. 2000-93462).

However, the above trunks-type disposable underpants 1 are complicated in construction and have had a problem in productivity.

In view of the above problem, an object of the present invention is to provide a wearing article which is simple and easy to produce, and a method for producing the same.

SUMMARY OF THE INVENTION

According to an aspect of the present invention, a wearing article is provided with a main body including a front part, a back part and a crotch part coupling the front and back parts. A shirring is so formed in a substantially widthwise middle portion of the crotch part of the main body as to shorten a space between the front and back parts. A ratio of the length of the crotch part along the forward and backward direction to a length between the pair of respective waist edges of the front and back parts is 1:15 to 1:2.

Such a wearing article is produced by cutting a web to make leg openings to thereby form the crotch part, attaching elastic members for waist to the web, forming the shirring in the crotch part along a direction intersecting with a feeding direction of the web, folding the web in two along the feeding direction of the web with the crotch part as a boundary and placing the front and back parts one over the other, and applying side sealing between adjacent crotch parts and cutting the sealed portion to complete a single wearing article. These and other objects, features, aspects, and advantages of the present invention will become more apparent from the following detailed description of the preferred embodiments/examples with reference to the accompanying drawings.

BRIEF DESCRIPTION OF THE DRAWINGS

FIGS. 1A to 1D show one example of an inventive wearing article, wherein FIG. 1A is a perspective view showing a worn state, FIG. 1B is a front view showing a state where the shirring of a crotch part is stretched, FIG. 1C is a plan view showing a developed state of a main body, and FIG. 1D is a side view of the main body of FIG. 1C.

FIGS. 2A to 2C show a wearing article according to a first embodiment, wherein FIG. 2A is a plan view showing a developed state, FIG. 2B is a side view of the wearing article in the state of FIG. 2A, and FIG. 2C is a section along A-A of FIG. 2A.

FIGS. 3A to 3C show a wearing article according to a second embodiment, wherein FIG. 3A is a plan view showing a developed state, FIG. 3B is a side view of the wearing article in the state of FIG. 3A, and FIG. 3C is a section along A-A of FIG. 3A.

FIGS. 4A to 4C show a wearing article according to a third embodiment, wherein FIG. 4A is a plan view showing a developed state, FIG. 4B is a side view of the wearing article in the state of FIG. 4A, and FIG. 4C is a section along A-A of FIG. 4A.

FIGS. 6A to 6F are plan views of a wearing article of a fourth embodiment showing attachment examples of elastic members for legs.

FIG. 10 is a perspective view showing a mechanism for inwardly displacing the crotch part by means of a needle member and a pressing member.

DETAILED DESCRIPTION OF THE PREFERRED EMBODIMENTS

Hereinafter, embodiments of the present invention are described in detail with reference to the accompanying drawings.

Figure 1A:
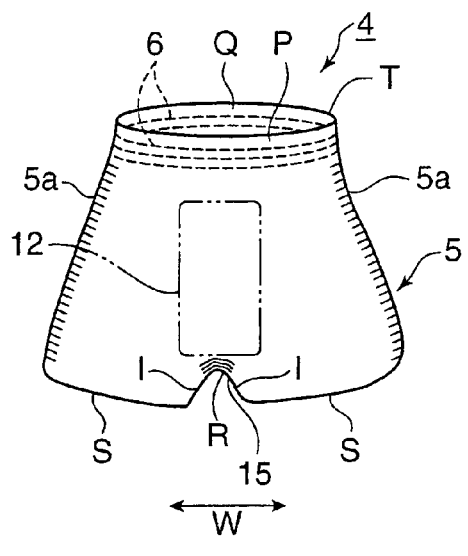
Figure 1B:
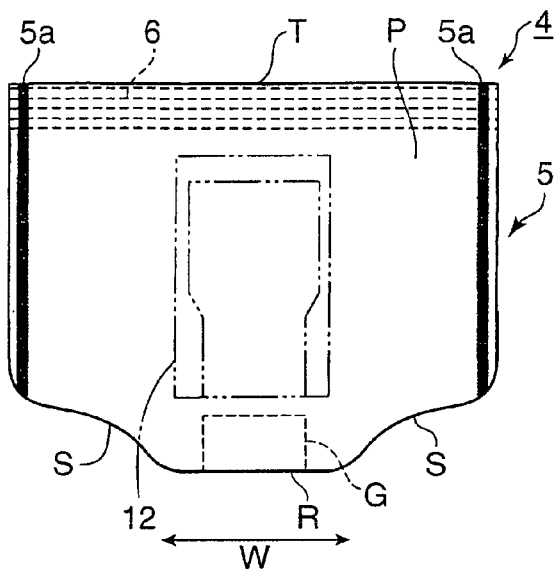
Figure 1C:
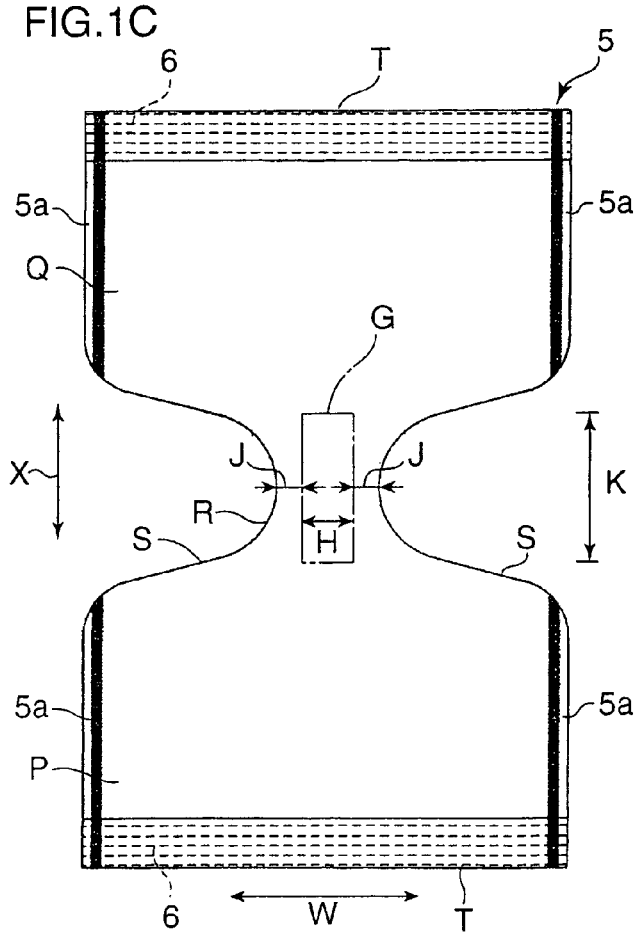
Figure 1D:
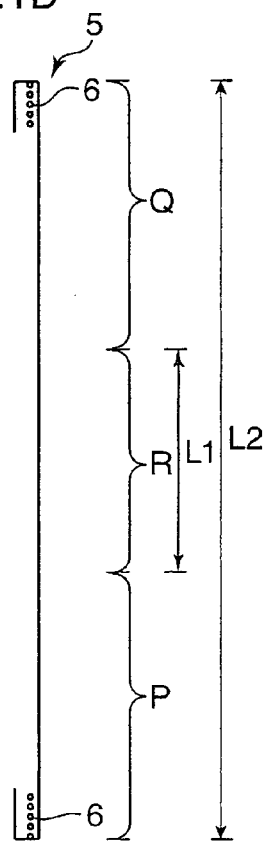

FIGS. 1A to 1D show a wearing article 4 (corresponding to 4A to 4D in FIGS. 2 to 4 and 6) as one example of an inventive wearing article, wherein FIG. 1A is a perspective view showing a worn state, FIG. 1B is a front view showing a state where the shirring of a crotch part is stretched, FIG. 1C is a plan view showing a developed state of a main body 5 (corresponding to 5A to 5D in FIGS. 2 to 4 and 6) with the shirring stretched, and FIG. 1D is a side view of the main body 5 of FIG. 1C.

As shown in FIG. 1A, the wearing article 4 includes the main body 5 comprised of a waist edge T corresponding to a body opening through which the trunk of the body passes upon wearing the wearing article 4, leg edges S corresponding to leg openings through which the legs pass upon wearing the wearing article 4, a front part P to be located at an abdomen side (front side) upon wearing the wearing article 4, a back part Q to be located at a back side (rear side) upon wearing the wearing article 4, and a crotch part R to be located at the crotch upon wearing the wearing article 4. The main body 5 takes the shape of trunks by applying side sealing to opposite end portions 5a of the front part P and the back part Q. The crotch part R includes leg portions I to be located below the forking of the crotch part R upon wearing the wearing article 4.

As shown in FIG. 1C, the front part P and the back part Q are coupled to each other by way of the crotch part R, and a pair of waist edges T and a pair of leg edges S are opposed to each other. In the developed state, length L1 of the crotch part R along the forward and backward direction X and length L2 of the main body 5 in the forward and backward direction X are set such that a ratio L1:L2 is 1:15 to 1:2. In order for the wearing article 4 to take the shape of trunks having a nice appearance, the ratio L1:L2 is preferably 1:4.4 to 1:3.8.

The crotch part R of the main body 5 is formed with shirring 15 (gathers, pleats, wrinkles or like wavy portions formed by making folds in the sheet material). The crotch part PR is pulled upward (direction from the leg openings toward the trunk opening) by this shirring 15 to form a gore upon wearing the wearing article 4.

The shirring 15 is so formed along a coupling direction of the front part and the back part in a middle portion of the crotch part R along widthwise direction W as to shorten a space between the front part P and the back part Q.

Specifically, as shown in FIGS. 1B and 1C, the shirring 15 is formed in a shirring forming section G. The shirring forming section G is set such that the area of the shirring forming section G does not exceed that of the crotch part; length K of the shirring 15 in the forward and backward direction (coupling direction of the front part P and the back part Q) does not exceed the length of the crotch part R in the forward and backward direction; and width H of the shirring forming section G is narrower than that of the crotch part R.

In order to take the shape of trunks or bloomers, shortest distance J between the leg edges S and the lateral edges of the shirring forming section G is preferably 5 mm or longer. Here, the widthwise direction W of the crotch part R means a direction connecting the pair of opposed leg edges S and corresponds to the widthwise direction W of the wearing article 4. The forward and backward direction X mean the coupling direction of the front part P and the back part Q (see FIG. 1C)

Elastic members 6 for waist are attached in widthwise direction W at portions of the front part P and the back part Q to be located around the trunk upon wearing the wearing article 4. In order to better fit the wearing article 4 to the body, elastic members for body fitting may be attached in widthwise direction at the front part P and/or the back part Q.

The wearing article 4 may be constructed such that an absorbent 12 is attached to the main body 5 if necessary.

Figure 2A:
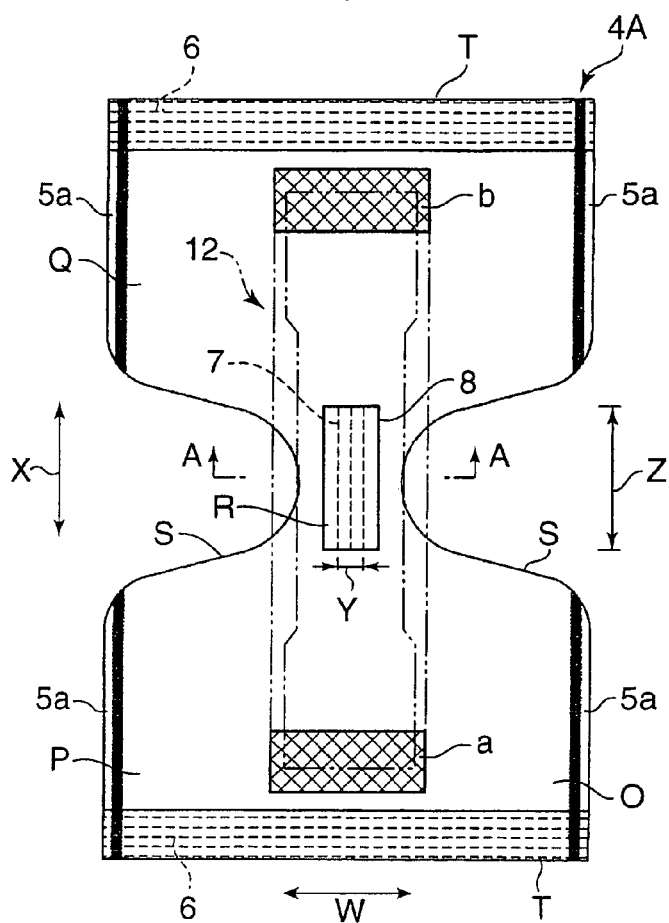
Figure 2B:
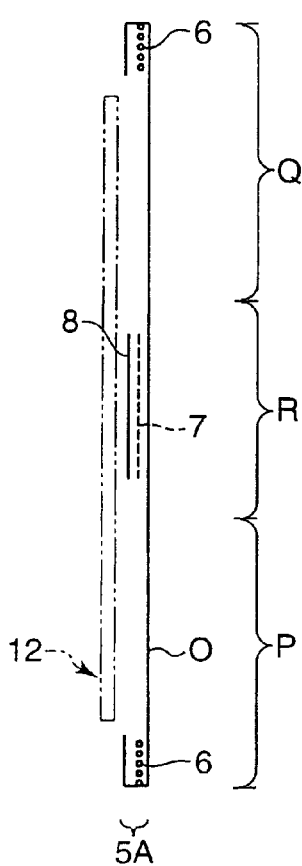
Figure 2C:
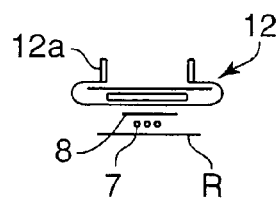

FIGS. 2A to 2C show a wearing article 4A of the trunks type according to the first embodiment, wherein FIG. 2A is a plan view showing a developed state with the shirring stretched, FIG. 2B is a side view of the wearing article of FIG. 2A, and FIG. 2C is a section along A-A of FIG. 2A. Although the absorbent 12 to be described later is shown in solid line in FIG. 2C, it is shown in phantom line in FIGS. 2A and 2B for the sake of convenience.

The wearing article 4A includes a main body 5A comprised of a waist edge T, a front part P, a back part Q, leg edges S and a crotch part R coupling the front part P and the back part Q, and the absorbent 12 if necessary. Elastic members 7 are attached under a stretched state in the forward and backward direction X substantially in a middle portion of the crotch part R along widthwise direction W.

Figure 5B:
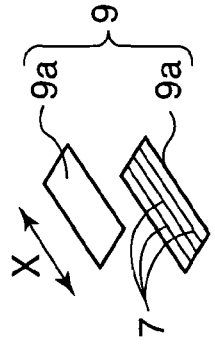
FIG. 5B is an exploded perspective view of an elastic sheet piece.
Figure 5C:
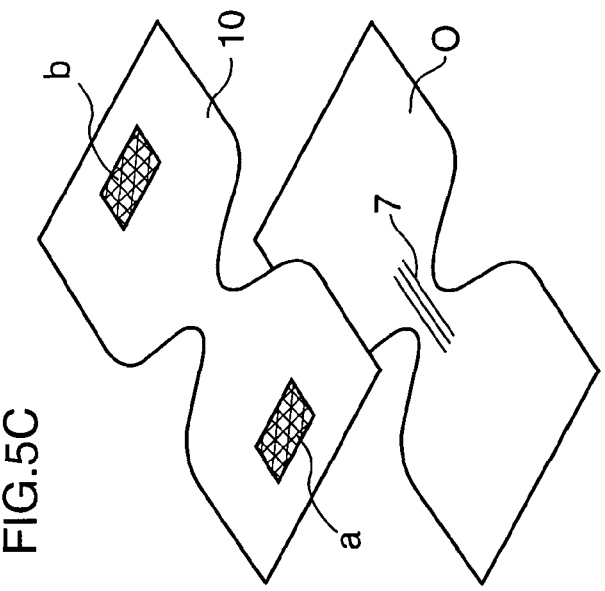
FIG. 5C is a perspective view of a sheet material of the third embodiment.
Figure 5A:
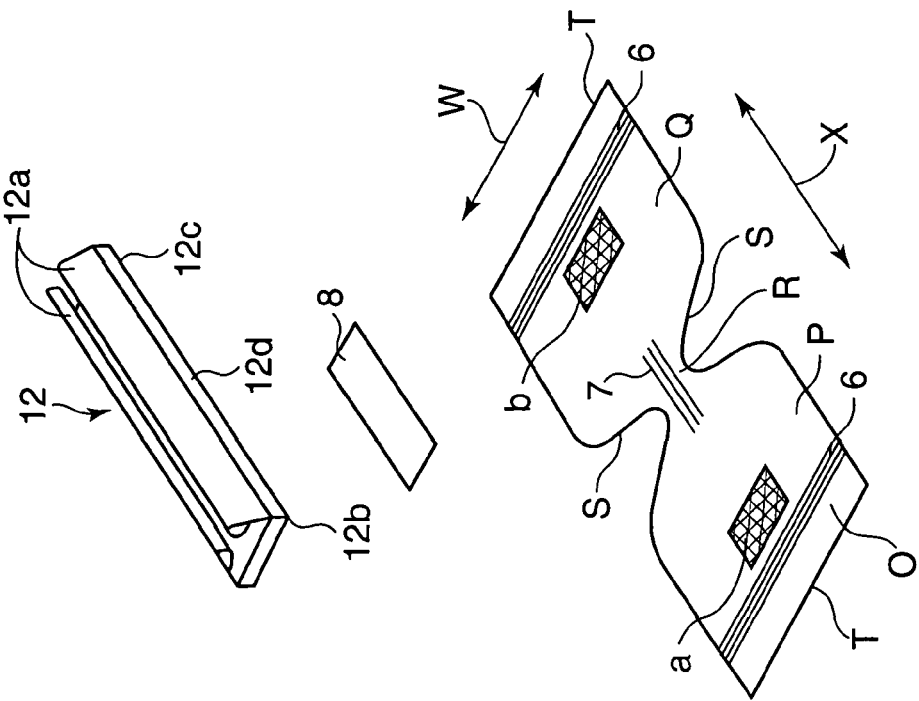
FIG. 5A is an exploded perspective view of the wearing article of the first embodiment.

As shown in FIG. 5A, an outer sheet O of the main body 5A is formed by forming leg openings along the leg edges S in a sheet material. Any material may be used as the sheet material for the outer sheet O provided that it is sheet-shaped. For a disposable wearing article having a touch and an appearance as an underwear, a nonwoven fabric is preferable.

The absorbent 12 is, if necessary, attached at positions a, b shown by crosshatching as shown in the aforementioned solid line or phantom line. The fixing positions a, b may be set in portions overlapping positions where elastic members 6 for waist are attached.

The wearing article 4A in the developed state comes to take the shape of trunks as shown in FIG. 1 by being folded in two with the crotch part R as a boundary to place the front part P and the back part Q one over the other and applying side sealing to opposite widthwise end portions 5a of the front and back parts P, Q. Although the width of the crotch part R is narrower than that of the absorbent 12 in FIG. 2A, it may be wider than that of the absorbent 12 as shown in FIG. 1A.

Here, the width of the absorbent 12 means the length of the absorbent 12 in a direction intersecting with the longitudinal direction of the absorbent 12 and, if the absorbent 12 does not take a rectangular shape, but takes another shape such as the shape of a sandglass, means the shortest length of the absorbent 12 in a direction intersecting with the longitudinal direction of the absorbent 12. The width of the crotch part R means the shortest length of the crotch part R along widthwise direction.

In a worn state, the wearing article 4A is formed with shirring 15 in the forward and backward direction X by shrinking forces of elastic members 7 for crotch (see FIG. 1A). This shirring 15 can also be formed by another method to be described later.

The elastic members 7 for crotch are adhered while being sandwiched between a sheet piece 8 having a length and a width larger than those of the elastic members 7 for crotch. A nonwoven fabric, a film or the like may be used as the sheet piece 8, but which material is used therefor does not matter as long as this material can sandwich the elastic members 7 for crotch in cooperation with the crotch part R.

In order for the wearing article 4A to retain in the shape of trunks, it is, for example, preferable that length Z in the forward and backward direction X of a section where the elastic members 7 for crotch are attached is equal to or shorter than the length of the crotch part R in the forward and backward direction X and width Y thereof is shorter than the width of the crotch part R. It is particularly preferable to set the width of this section as narrow as possible. The length X is suitably set, for example, at 40 to 350 mm in a stretched state although depending on a stress during the extension of an elastic material used. The length X is suitably 60 to 350 mm if the wearing article 4A is for adults while being suitably 40 to 220 mm if it is for children.

The width Y of the section where the elastic members 7 for crotch are attached can be set, for example, within the range of from the width of one elastic member of 230 dTex to 70 mm. Here, the stretching degree of the elastic members 7 for crotch is 1.1 to 5 times. As described later, the outer sheet O may be made of two sheets, and the elastic members 7 for crotch may be attached to the crotch R of the outer sheet O while being sandwiched between these two sheets, or the elastic members 7 for crotch may be singly attached to the outer sheet O.

The elastic members may be so attached as to extend from the crotch part R to the front part P and/or the back part Q. However, in such a case, such a treatment as to prevent the shrinking forces of the elastic members of the front part P and/or the back part Q from acting is preferably applied for the better appearance of the wearing article 4A.

In the case of forming the shirring 15 by the other method to be described later, the shirring 15 is dimensioned such that the length K thereof along the forward and backward direction (coupling direction of the front part P and the back part Q) does not exceed the length L1 of the crotch part R along the forward and backward direction and the width H thereof is shorter than the width of the crotch part R.

In order for the wearing article 4A to take the shape of trunks, the width H of the shirring 15 is preferably 70 mm or shorter and the length K along the forward and backward direction in a state where the shirring 15 is formed is preferably 250 mm or shorter. In order for the wearing article 4A to take the shape of trunks having a nice appearance, it is preferable, for example, to set the width H of the shirring 15 at 24 mm or shorter for adults and at 16 mm or shorter for children and to set the length K along the forward and backward direction at 10 to 200 mm.

An elastic material such as flat rubber, rubber threads, elastic threads made of polyurethane (e.g. LYCRA), elastic films made of polyurethane or elastic films made of polyolefin or an elastic hot melt can be used as the material for the elastic members 7 for crotch. One elastic member 7 may be used or a plurality of elastic members 7 may be used together. The formation of the shirring 15 by one thread-shaped elastic member for crotch is preferable since the width H of the shirring 15 is as narrow as possible, which enables the shape of trunks having a nice appearance. Elastic members 6 for waist and elastic members 13a, 13b for legs to be described later are made of a similar material.

With reference to FIG. 5A, the absorbent 12 is formed to have a rectangular shape long along the forward and backward direction X and constructed such that an absorbent core is sandwiched between a liquid impermeable backing sheet and a liquid permeable top sheet although not specifically shown. Standing flaps 12a are provided at the opposite sides of the absorbent 12.

The absorbent 12 may take the shape of a sandglass or the like, and may suitably adopt the shape and construction used in this technological field. It should be noted that the absorbent 12 may be wider or narrower than the crotch part P in a state where the crotch part R is stretched.

The opposite ends (front portion 12b and rear portion 12c) of this absorbent 12 with respect to longitudinal direction are attached at the crosshatched positions a, b of the main body 5. Although the fixing positions are defined on the inner side of the main body 5 (side to face a wearer) in FIG. 5A, the absorbent 12 may be attached such that the opposite ends thereof with respect to longitudinal direction are located on the outer side of the main body (side not to face a wearer). The absorbent 12 may be attached by being adhered using a hot melt adhesive or a double-coated adhesive tape or by being exchangeably attached using a mechanical fastener or the like.

The absorbent 12 may also be attached by placing the front and rear portions 12b, 12c of the absorbent 12 at positions where the elastic members 6 for waist are attached and folding portions of the sheet material to be located around the trunk to sandwich the front and rear portions 12b, 12c.

Figure 15:
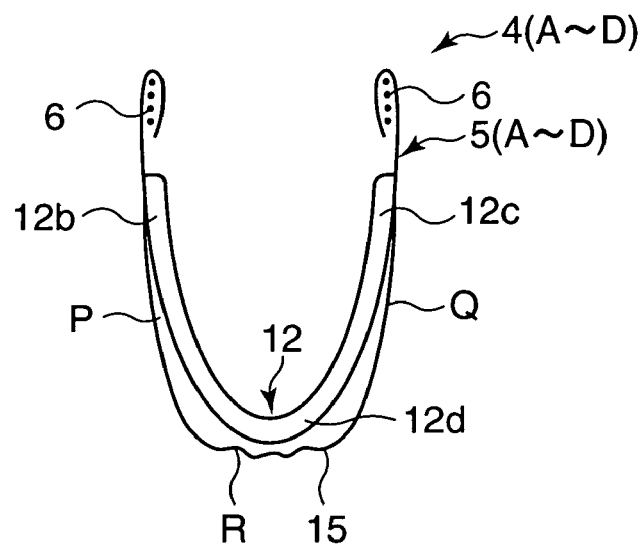
FIG. 15 is a side view in section showing a wearing article.
Figure 16:
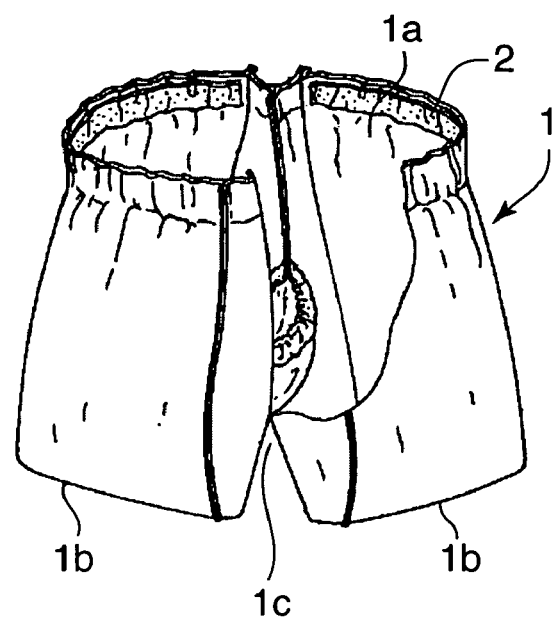
FIG. 16 is a perspective view showing a worn state of conventional disposable underpants of the trunks type.

An intermediate portion 12d of this absorbent 12 may be separated from a section of the crotch part R where the elastic members 7 for crotch are attached without being attached to the crotch part R (see FIG. 15) or may be attached along the crotch part R. Alternatively, the absorbent 12 may be attached to the crotch part R by the above method.

Figure 7:
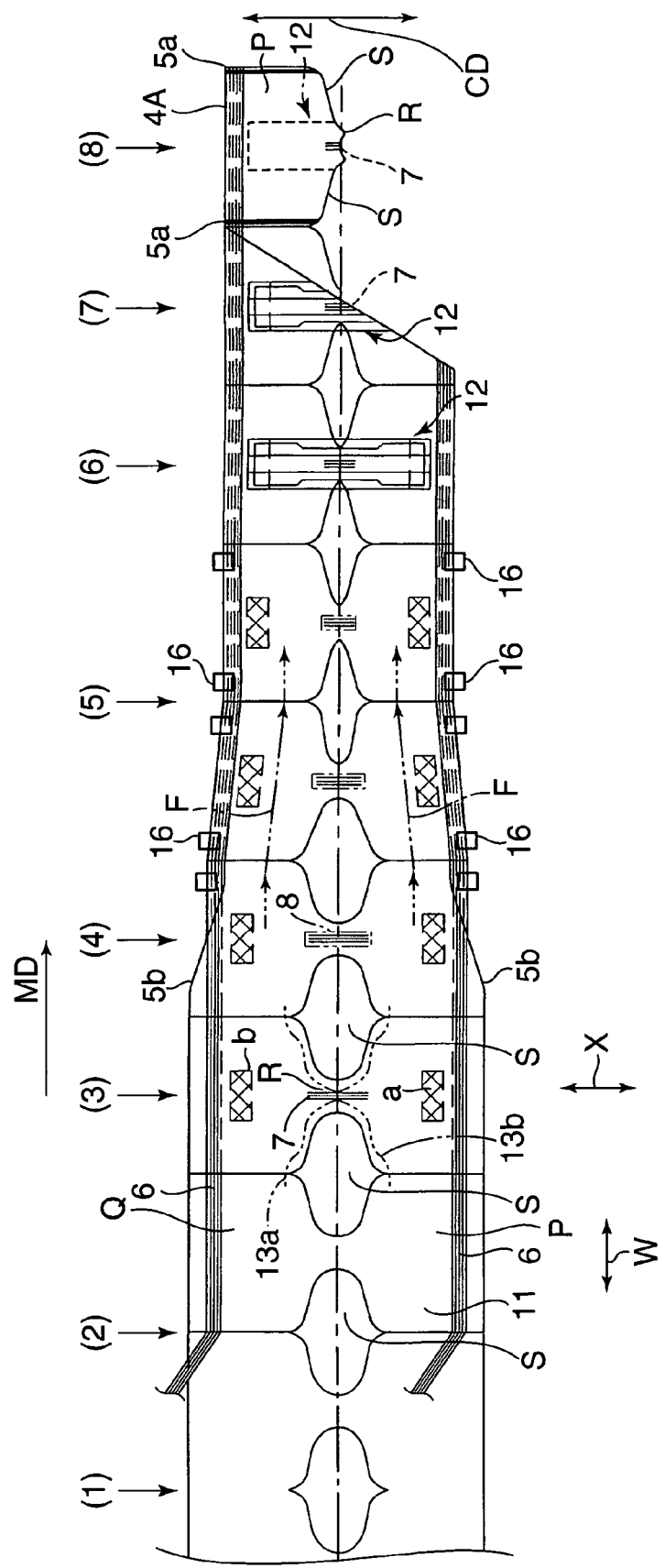
FIG. 7 is a diagram showing a manufacturing process of the wearing articles of the first embodiment.

The wearing article 4A of the first embodiment can be produced, for example, by a process as shown in FIG. 7 (first example).

Leg openings are made in step (1) while a web 11 for the outer sheet is continuously fed in a feeding direction (MD). In step (2), the elastic members 6 for waist are attached along the feeding direction (MD) under a stretched state to parts of the web 11 at the inner sides of the opposite ends 5b with respect to a direction (CD) intersecting with the feeding direction. The feeding direction (MD) corresponds to the widthwise direction W of the crotch part R of the wearing article 4A, and the direction (CD) intersecting with the feeding direction (MD) corresponds to the forward and backward direction X (coupling direction of the front part P and the back part Q) of the wearing article 4A.

In step (3), the elastic members 7 for crotch are attached to a substantially widthwise middle portion of the crotch part R under a stretched state along the direction (CD) intersecting with the feeding direction. In step (4), the elastic members 7 for crotch are adhered by being sandwiched between the sheet piece 8 and the crotch part R, and the elastic members 6 for waist are held in and adhered by folding the opposite ends 5b of the web 11 inwardly. The step of folding the opposite ends of the web 11 inwardly may be carried in step (2) as well. It is also possible to attach the elastic members 7 for crotch to the crotch part R before the leg openings are made. In the case of attaching the elastic members 6 for waist to the opposite end portions 5b, the step of folding the opposite end portions 5b of the web 11 inwardly can be omitted.

Figure 14A:
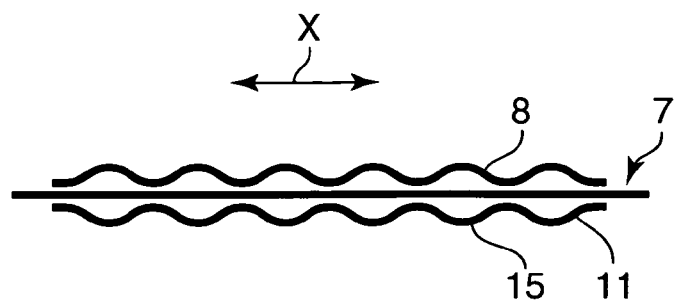
FIGS. 14A to 14D are side views showing the shirring formed by elastic members for crotch, the shirring formed by adhering a sheet material to the wavy portion, the shirring formed by applying a synthetic resin to the wavy portion, and the shirring formed by heating and melting the wavy portion, respectively.

In step (5), the shirring 15 is formed. The shirring 15 can be formed using only the shrinking forces of the elastic members 7 for crotch. However, in the case of producing the wearing article 4A at high speed or in the case of desiring to strictly control the length of the shirring 15, it is preferable, in addition to the use of the shrinking forces of the elastic members 7 for crotch, that the opposite end portions 5b of the web 11 are gripped by gripping means 16 (gripping members to be described later or the like) and the web 11 is displaced inwardly while forcibly moving the gripping means 16 inwardly (see arrow F), thereby forming the shirring 15 in the crotch part R between step (4) and step (5) [see FIG. 14A. the forward and backward direction X in FIG. 14 correspond to the direction (CD) intersecting with the feeding direction of the web 11.]

Here, to displace inwardly means to shorten the length of the web 11 in the direction intersecting with the feeding direction by displacing the web 11 along the direction (CD) intersecting with the feeding direction. The "inward displacement" means a movement toward the center along the direction (CD) intersecting with the feeding direction. The web 11 may be displaced inwardly by moving both gripping means 16 at the opposite sides of the web 11 toward each other along the direction (CD) intersecting with the feeding direction or by moving one gripping member 16 toward the other gripping member 16 that is attached. It should be noted that the gripping means 16 can be displaced inwardly by means of conveyors 17 to be described later or the like.

Subsequently, in step (6), the absorbent 12 is attached at the fixing positions a, b.

In step (7), the web 11 is folded in two along the feeding direction thereof with the crotch part R as a boundary to place the front part P and the back part Q one over the other such that the elastic members 6 for waist on the front part P and the back part Q face each other. In step (8), side sealing is applied to the opposite end portions 5a of the front parts P and the back parts Q between adjacent crotch parts R and the web 11 is cut between adjacent opposite end portions 5a, whereby the wearing article 4A of the trunks type as a single article as shown in FIG. 1 is completed.

For the wearing article 4A requiring no absorbent 12, step (6) can be omitted.

In the wearing article 4A of the trunks type as described above, the shirring 15 is formed using the shrinking forces of the elastic members 7 for crotch attached to the substantially widthwise middle portion of the crotch part R, whereby the substantially widthwise middle portion of the crotch part R is tightened along the forward and backward direction X as shown in FIG. 1B, the crotch part R is pulled up (direction extending from the leg openings toward the trunk opening upon being worn) to form a gore, and the wearing article 4A comes to take the shape of trunks. Therefore, the wear comfort and the appearance upon wearing the trunks are improved.

If the shirring 15 is formed by attaching the elastic members 7 for crotch to the substantially widthwise middle portion of the crotch R as above, trunks having a simple construction can be manufactured at a lower cost.

Further, by adhering the elastic members 7 for crotch between the outer sheet O of the wearing article 4A and the sheet piece 8, at least the main body 5A of the wearing article 4A can be produced from one web 11. Thus, the construction of the wearing article 4A can be simplified to enable the lower-cost production.

In the case of providing no absorbent 12, the wearing article 4A can also be used as disposable underpants for travel in addition to being used as pants-shaped diaper or training pants for children or incontinence underpants for adults.

In the case that the absorbent 12 is attached to the main body 5A, the wearing article 4A can be used as pants-shaped diaper or training pants for children or incontinence underpants for adults.

The absorbent 12 is distanced from the section of the crotch part R where the elastic members 7 for crotch are attached, i.e. the intermediate portion 12d of the absorbent 12 is distanced from the elastic members 7 for crotch, and consequently the shrinking forces of the elastic members 7 for crotch do not act on the absorbent 12. Thus, the absorbent 12 is unlikely to be wrinkled due to shrinkage. Further, even in the case that the absorbent 12 is attached to the crotch part R, the absorbent 12 is unlikely to be wrinkled due to shrinkage since the absorbent 12 is attached after the shrinkage of the elastic members 7 for crotch.

If the absorbent 12 is exchangeably attached, the wearing article 4A can be repeatedly used only by exchanging the absorbent 12. Thus, the wearing article 4A can be economically used.

Figure 3A:
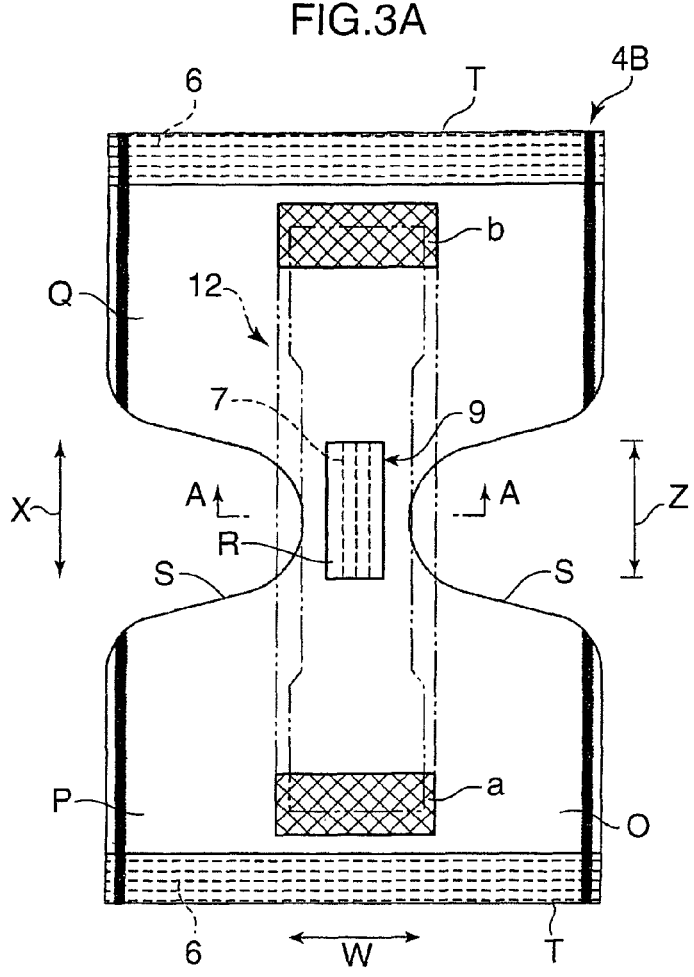
Figure 3B:
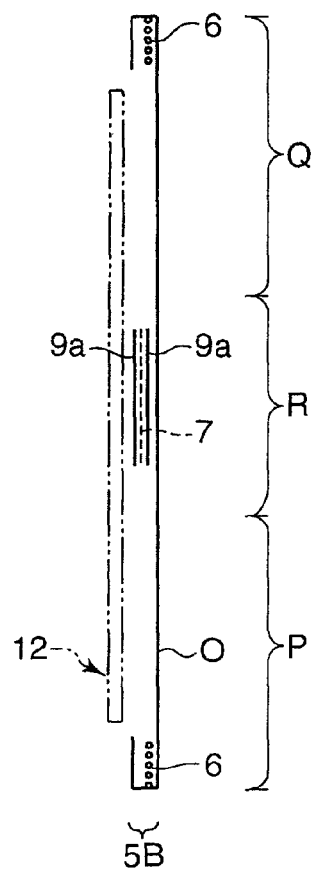
Figure 3C:
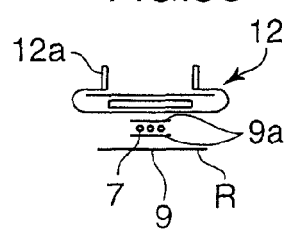

FIGS. 3A to 3C show a wearing article 4B according to a second embodiment, wherein FIG. 3A is a plan view showing a developed state with the shirring stretched, FIG. 3B is a side view of the wearing article 4B in the state of FIG. 3A, and FIG. 3C is a section along A-A of FIG. 3A.

The wearing article 4B differs from the wearing article 4A of the first embodiment in that an elastic sheet piece 9 formed by attaching the elastic members 7 for crotch under a stretched state between two upper and lower sheet pieces 9a and cut to a specified length as shown in FIG. 5B is so adhered to the crotch part R of the outer sheet O as to elongate and shrink in the forward and backward direction X instead of attaching the elastic members 7 for crotch between the outer sheet O and the sheet piece 8.

The elastic sheet 9 may be formed by adhering the elastic members 7 for crotch under a stretched state to one sheet piece instead of being formed using the two upper and lower sheet pieces 9a, and may be adhered to the crotch part R of the outer sheet O.

Since it is sufficient to adhere the elastic sheet piece 9 to the crotch part R in this wearing article 4B, the wearing article 4B can be produced from one web 11 similar to the wearing article 4A. Thus, the construction of the wearing article 4A can be simplified to enable the lower-cost production.

FIGS. 4A to 4C show a wearing article 4C according to a third embodiment, wherein FIG. 4A is a plan view showing a developed state with the shirring stretched, FIG. 4B is a side view of the wearing article 4C in the state of FIG. 4A, and FIG. 4C is a section along A-A of FIG. 4A.

The wearing article 4C differs from the wearing article 4A of the first embodiment in that the elastic members 7 for crotch are adhered between the outer sheet O of the wearing article 4C and a sheet material 10 having substantially the same shape as the outer sheet O of the wearing article 4C while being stretched in the forward and backward direction X as shown in FIG. 5C instead of using the sheet piece 8. The fixing positions a, b of the absorbent 12 are set not on the outer sheet O of the wearing article 4C, but on the sheet material 10.

FIGS. 6A to 6F are plan views of a main body 5D of a wearing article 4D of the bloomers type according to a fourth embodiment in a developed state. Unless specifically shown, the construction and the material used are similar to those of the wearing articles 4A to 4C of the trunks type according to the first to third embodiments, and the shape of the shirring 15 is also similar. Although not shown in FIG. 6, the absorbent 12 (see FIG. 5A) may be attached to the main body 5D similar to the wearing articles of the first to third embodiments in the wearing article 4D of the bloomers type or the main body 5D may serve as the wearing article 4D without attaching the absorbent 12.

The wearing article 4D of the bloomers type according to this embodiment differs from the wearing articles 4A to 4C of the trunks type according to the first to third embodiments in that elastic members 13a, 13b for legs are attached while being stretched along the leg edges S.

These elastic members 13a, 13b for legs may be attached while being stretched along the leg edges S as shown in phantom, for example, between step (2) and step (3) in the manufacturing process of FIG. 7.

FIG. 6A shows an example in which the elastic members 13a, 13b for legs are attached while crossing in X at the crotch part R. FIG. 6B shows an example in which the elastic members 13a, 13b for legs of FIG. 6A are cut "c" at a substantially middle portion of the crotch part R along widthwise direction W to reduce shrinking forces in widthwise direction W in this portion. The shrinking forces may be reduced by cutting the elastic members 13a, 13b for legs by means of a cutting blade fitted on a roller or by embossing or heat embossing.

FIG. 6C shows an example in which the elastic members 13a, 13b for legs are attached in U-shape while crossing at the crotch part R. FIG. 6D shows an example in which the elastic members 13a, 13b for legs of FIG. 6C are cut "c" at the substantially middle portion of the crotch part R along widthwise direction W to reduce shrinking forces in widthwise direction W in this portion.

FIG. 6E shows an example in which the elastic members 13a, 13b for legs are attached in U-shape without crossing at the crotch part R. FIG. 6F shows an example in which the elastic members 13a, 13b for legs of FIG. 6E are cut "c" at the substantially middle portion of the crotch part R along widthwise direction W to reduce shrinking forces in widthwise direction W in this portion.

The wearing article 4D of the bloomers type is particularly suitable for women, and the leg edges 3 are better fitted to the legs of a wearer due to the shrinking forces of the elastic members 13a, 13b for legs in addition to the effects of the respective wearing articles 4A to 4C of the trunks type. Thus, the wear comfort and the appearance upon wearing the wearing article 4D are improved. Further, by reducing the shrinking forces of the elastic members 13a, 13b for legs, the shrinking forces acting in widthwise direction W are reduced in the corresponding portion so as not to influence the elastic members 7 for crotch.

In the wearing articles 4A to 4D of the respective embodiments, the shrinking forces of the elastic members 7 for crotch attached to the crotch part R are utilized in order to form the shirring 15 in the substantially widthwise portion of the crotch part R. However, the shirring 15 may be formed by another method.

Figure 8:
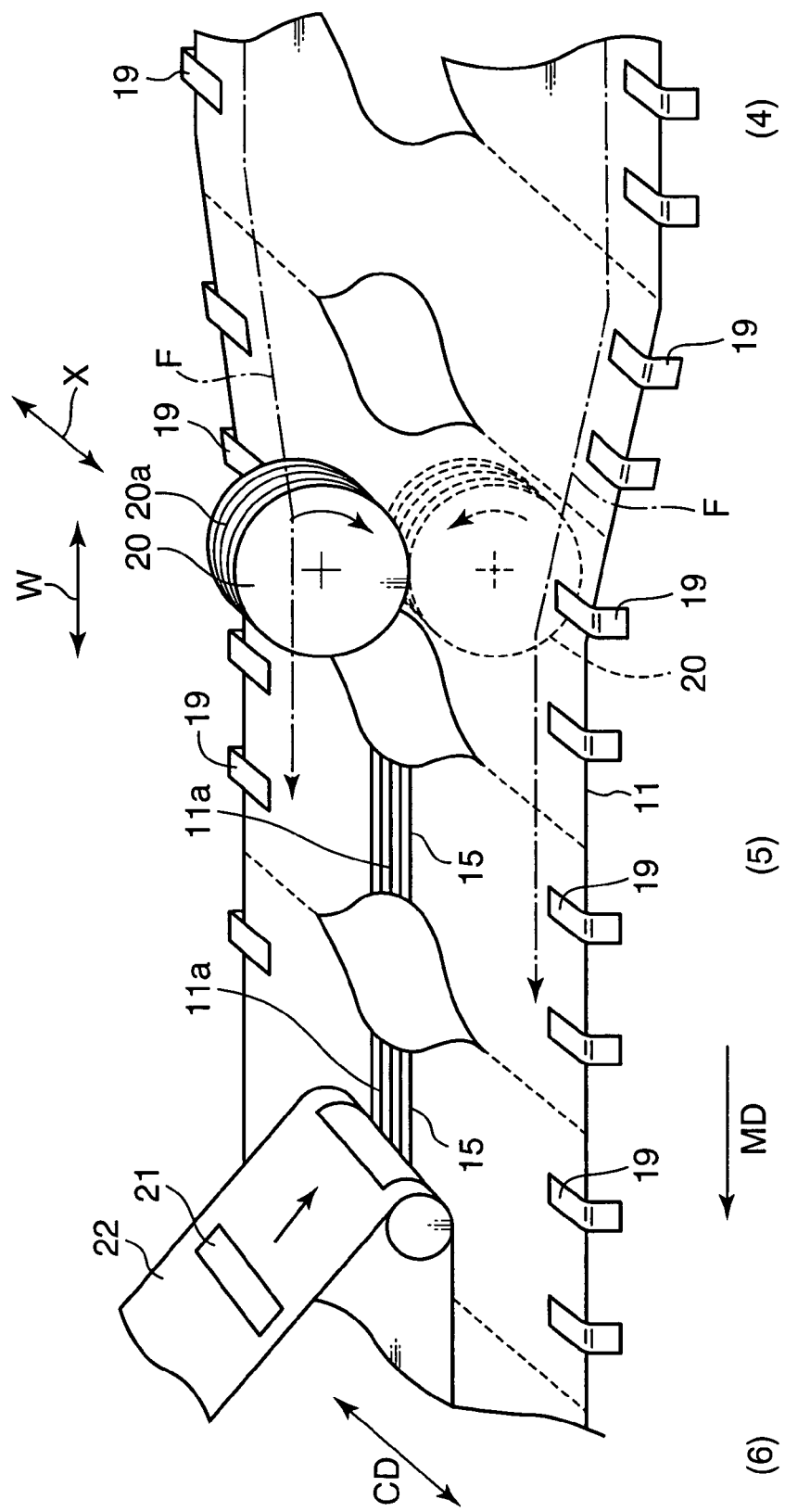
FIG. 8 is a perspective view showing a mechanism for folding the crotch part inwardly and a mechanism for forming a wavy portion.
Figure 9A:
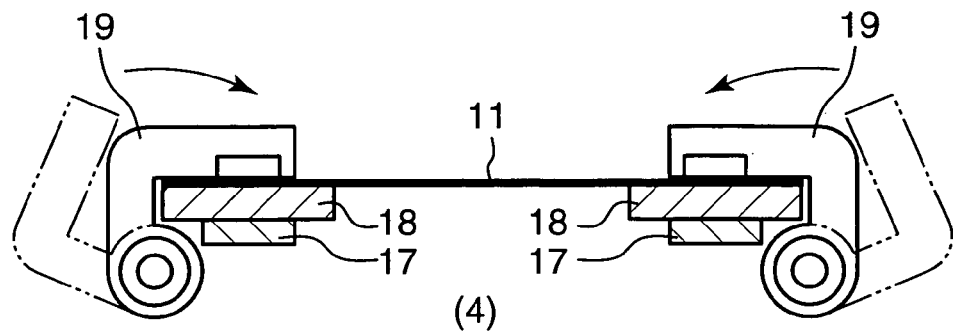
FIGS. 9A and 9B are side views showing inward displacing tables and holding claws before and after the inward displacements.

Specifically, according to a second example of the method for forming the shirring 15, the shirring is mechanically formed as shown in FIGS. 8 and 9 without utilizing the shrinking forces of the elastic members 7 for crotch. Thus, the formed shirring 15 is not stretchable. Reference numerals (4), (5), (6) in FIG. 8 correspond to reference numerals (4), (5), (6) (steps (4), (5), (6) in the first example) in FIG. 7.

In order to inwardly displace the web 11 between step (4) and step (5) (see phantom-lined arrows F), a pair of left and right conveyors 17 are provided, on a production line, at positions corresponding to the opposite ends of the web 11 with respect to the direction (CD) intersecting with the feeding direction. Inward displacing tables 18 are mounted on the respective conveyors 17, and gripping claw members 19 for pressing the opposite sides of the web 11 against the upper surfaces of the inward displacing tables 18 to grip them are provided on the inward displacing tables 18. The conveyors 17 are so laid as to gradually narrow a spacing therebetween while moving in the feeding direction (MD) of the web 11.

The web 11 having the opposite ends thereof gripped between the gripping claw members 19 and the inward displacing tables 18 is forcibly inwardly displaced along the direction (CD) intersecting with the feeding direction between step (4) and step (5) while being conveyed in the feeding direction (MD) together with the conveyors 17.

Figure 9B:
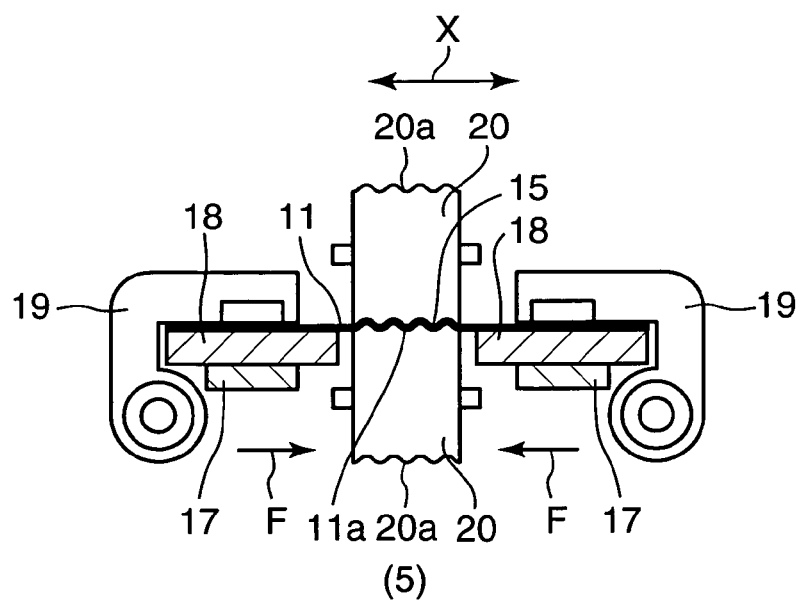

A pair of upper and lower embossing rollers 20 are arranged at a position corresponding to the substantially widthwise middle portion of the crotch part R of the main body between step (4) and step (5) as shown in FIG. 9B. Each embossing roller 20 is formed with grooves 20a wavy in the forward and backward direction X so as to form wavy part 11a, i.e. the shirring 15 in the web 11.

Figure 14B:
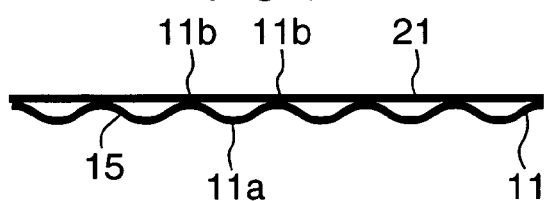

A sheet material conveyor 22 for adhering a shirring shape retaining sheet material 21 to ridges 11b of the wavy part 11a as shown in FIG. 14B in order to retain the shape of the wavy part 11a of the web 11 is provided between step (5) and step (6).

A nonwoven fabric, a film or the like can be used as the sheet material 21. It does not, in fact, matter which material is used provided that this material is sheet-shaped.

It is sufficient for the sheet material 21 to have such a size capable of forming the shirring 15, i.e. capable of retaining the shape of the wavy part 11a. Instead of the sheet material, a thread-shaped material can also be used.

Figure 14C:
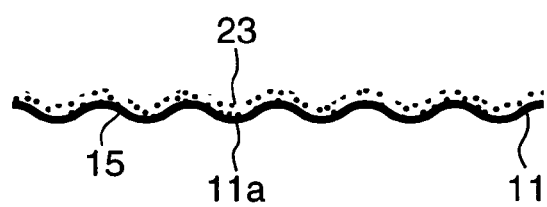

Instead of adhering the sheet material 21 in order to retain the shape of the wavy part 11a of the web 11, a synthetic resin material 23 may be applied to the wavy part 11a and solidified as shown in FIG. 14C.

It is sufficient to apply the synthetic resin material 23 within such a range capable of forming the shirring 15, i.e. capable of retaining the shape of the wavy part 11a. Line application, surface application or the like can be raised as a way of application. In the case of surface application, it is preferable that an area of application does not exceed the area of the shirring forming section G (see FIG. 1C). Line application is preferable in order to better the appearance of the wearing articles 4A to 4D of the trunks and bloomers types.

Figure 14D:
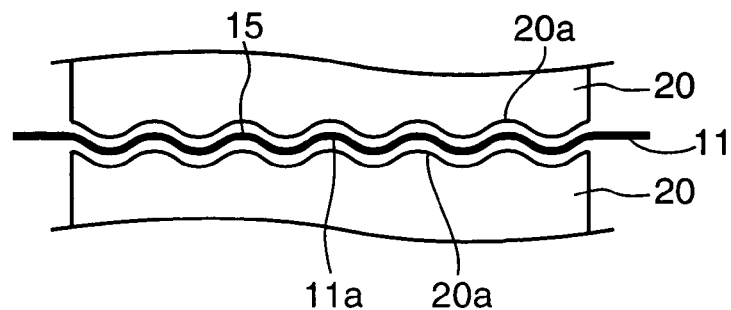

Likewise, as shown in FIG. 14D, the embossing rollers 20 may be provided with heating sections, so that the wavy part 11a is heated to be melted and solidified or thermally set while being formed. In the case of melting and solidifying or thermally setting by heating, a thermoplastic material such as PP (polypropylene), PE (polyethylene), PET (polyethylene terephthalate), nylon or a compound material of these can be suitably used as the material for the web 11.

In the embodiment shown in FIGS. 8 and 9, the gripping claw members 19 as the gripping means are provided on the inward displacing tables 18. Instead of the gripping claw members 19, frog-shaped needle members 24 are provided on the inward displacing tables 18 as shown in FIGS. 10 and 11, and pressing members 25 in the form of brush rollers for pressing the web 11 to let the need members 12 pierce through the web 11 to grip the web 11 are provided at a location of step (4).

Figure 12:
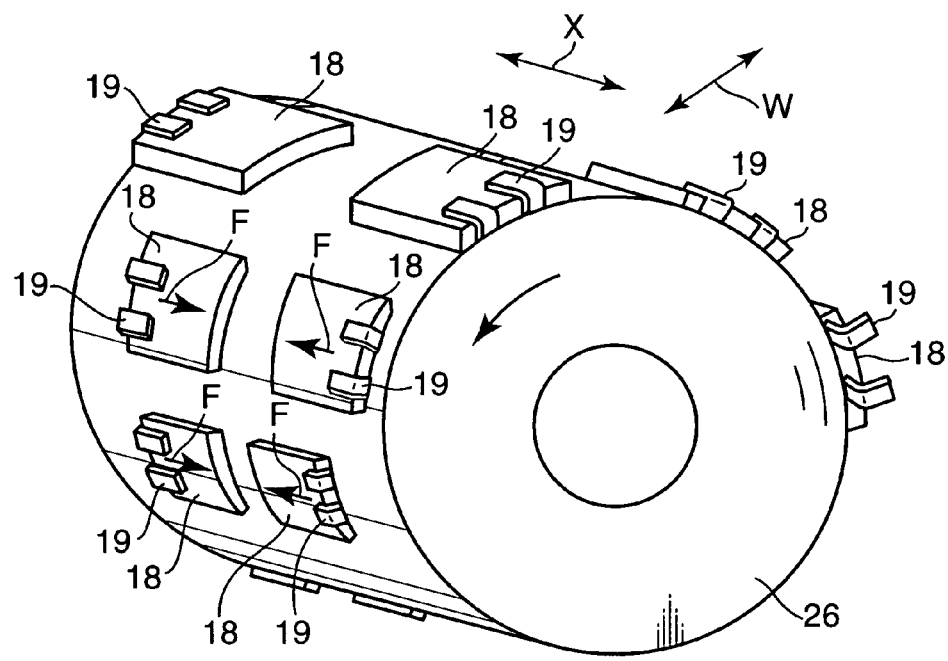
FIG. 12 is a perspective view of a drum having inward displacing tables.

Further, as shown in FIG. 12, a drum 26 rotating at the same circumferential speed as the conveyors 17 may be provided at an intermediate position of the conveyors 17 and the inward displacing tables 18 having the gripping claw members 19 may be so provided on the outer circumferential surface of this drum 26 as to be inwardly displaceable (see arrows F). The inward displacing tables 18 may be moved as instructed by guides (not shown) formed on the drum 26. Alternatively, cams and linking mechanisms may be, for example, provided.

Figure 11A:
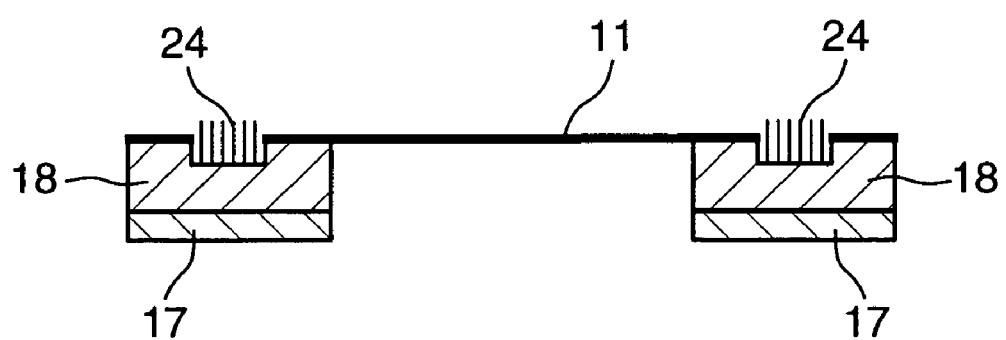
FIGS. 11A and 11B are side views showing inward displacing tables and needle members before and after the inward displacements.
Figure 11B:
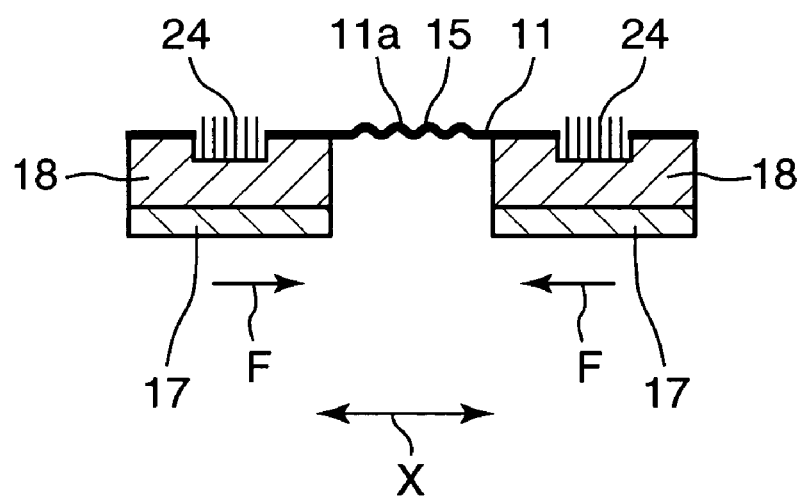

Instead of providing the inward displacing tables 18 with the gripping claw members 19, the construction as shown in FIGS. 10 and 11 may be adopted.

Figure 13:
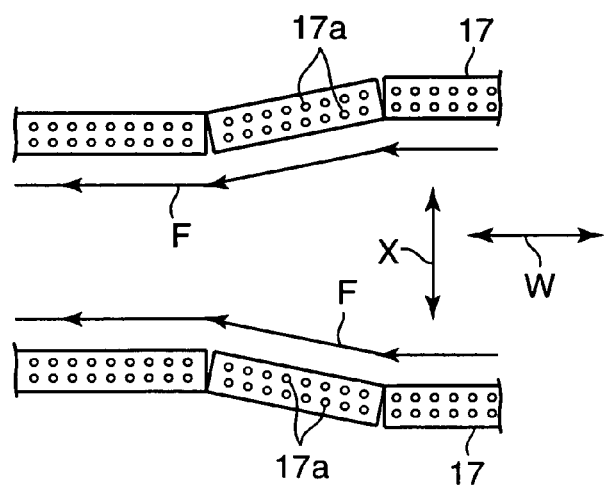
FIG. 13 is a plan view of conveyors having inward displacing tables.

Further, without providing the inward displacing tables 18, vacuum holes 17a for gripping the web 11 by suction may be formed in a pair of left and right conveyors 17 laid in such a manner as to inwardly displace (see arrows F), thereby gradually narrowing the spacing therebetween as shown in FIG. 13. Each conveyor 17 may be so constructed as to make a curving movement or may be divided into a plurality of conveyors.

According to the respective producing methods described above, the shirring 15 can be easily formed at a lower cost in the substantially widthwise middle portions of the crotch parts R in the continuous high-speed production line.

Further, if the embossing rollers 20 are used, the beautifully shaped shirring 15 can be more easily and securely formed.

Furthermore, if the crotch parts R are forcibly inwardly displaced by inwardly displacing the web 11 by the gripping means such as the gripping claw means 19, the folds can be quickly and securely made in the substantially widthwise middle portion of the crotch part R in the continuous high-speed production line.

The gripping means can be constructed by the gripping claw members 19 or a combination of the needle members 24 and the pressing members 25, and the inward displacing tables 18 can be provided on the conveyors 17 or the drum 26. Alternatively, the gripping means in the form of the vacuum holes 17a can be formed in the conveyors 17 capable of inwardly displacing. Therefore, the shirring 15 can be easily and securely formed in the substantially widthwise middle portions of the crotch parts R in the continuous high-speed production line.

As described above, a wearing article comprises a main body including a front part, a back part and a crotch part coupling the front and back parts. The main body includes a pair of waist edges opposed to each other and a pair of leg edges opposed to each other. A shirring is so formed in a substantially widthwise middle portion of the crotch part of the main body as to shorten a space between the front and back parts. A ratio of the length of the crotch part along the forward and backward direction to a length between the pair of waist edges is 1:15 to 1:2.

The shirring may be preferably formed by making folds in the substantially widthwise middle portion of the crotch part of the main body to shorten the substantially widthwise middle portion in a direction coupling the front and back parts and by retaining the wavy shape of the substantially widthwise middle portion.

The shirring may be preferably formed by the shrinking force of an elastic member for crotch attached to the substantially widthwise middle portion of the crotch part of the main body under a stretched state in a direction coupling the front and back parts.

Elastic members for legs may be preferably attached along the leg edges under a stretched state. An absorber may be preferably attached to the main body. A gore may be preferably formed at the crotch part by the shirring when the wearing article is worn.

The wearing article may be a wearing article of the trunks type suitable for men. In this case, no elastic member for legs is attached along the leg openings.

The crotch part may be tightened along the forward and backward direction or in the direction coupling the front and back parts by the shirring (gathers, pleats, wrinkles or like wavy portions formed by making folds in the sheet material) formed in the substantially widthwise middle portion of the crotch part of the main body. Thus, the crotch part is pulled up in the direction extending from the leg openings toward a trunk opening to form a gore when the wearing article is worn, and the wearing article comes to take the shape of trunks. Therefore, the wear comfort and the appearance when the wearing article is worn are improved.

Since the crotch part is pulled up to form the gore by forming the shirring in the crotch part in this way, the wearing article having a simple construction can be produced at a lower cost.

In the case where no absorber is attached, this wearing article can be used as disposable underpants for travel other than being used as a pants-type diaper or training parts for infants and small children or incontinence underpants for adults.

Further, if the ratio of the length of the crotch part along the forward and backward direction to the length between the pair of waist edges is 1:15 to 1:2, the wearing article takes the shape of trunks having a nice appearance.

If the shirring of the above wearing article is formed by making folds in the substantially widthwise middle portion of the crotch part of the main body to shorten the substantially widthwise middle portion in a direction coupling the front and back parts and by retaining the wavy shape of the substantially widthwise middle portion, the substantially widthwise middle portion of the crotch part is tightened along the forward and backward direction and is pulled up to form a gore, and the wearing article can take the shape of trunks.

If the shirring of the above wearing article is formed by the shrinking force of an elastic member for crotch, the substantially widthwise middle portion of the crotch part is tightened along the forward and backward direction and is pulled up to form a gore, and the wearing article can take the shape of trunks.

Also, the wearing article may be a wearing article of the bloomers type in which elastic members for legs are attached along the leg openings of the wearing article of the trunks type and particularly suitable for women. Similar to the above wearing article of the trunks type, the crotch part may be tightened along the forward and backward direction by the shirring formed in the substantially widthwise middle part of the crotch part of the main body. When this wearing article is worn, the crotch part is pulled up to form a gore, thereby forming leg portions. Therefore, the wear comfort and the appearance when this wearing article is worn are improved.

Since the leg openings closely fit the legs of a wearer due to the shrinking forces of the elastic members for legs in such a wearing article of the bloomers type, the wear comfort and the appearance when the wearing article is worn are improved. Further, a leakage through the leg portions can also be prevented.

In the case that the elastic members for legs of the above wearing article cross the crotch part, the shrinking forces acting in widthwise direction are reduced in the crotch part to give no influence on the elastic member for crotch if the shrinking forces of the elastic members for legs are reduced.

The wearing article may be used as a pants-type diaper or training parts for infants and small children or incontinence underpants for adults if the opposite ends of an absorber with respect to the longitudinal direction thereof are attached to the main body.

If the absorber is exchangeably attached in the wearing article, the main body can be repeatedly used only by exchanging the absorber. Thus, the wearing article can be economically used.

The shape of the wavy portion of the wearing article can be easily and inexpensively retained in a production line.

A wearing article is produced by cutting a web to make leg openings to thereby form the crotch part, attaching an elastic member for waist to the web, forming a shirring in the crotch part along a direction intersecting with a feeding direction of the web, folding the web in two along the feeding direction of the web with the crotch part as a boundary to form front and back parts placed on one over the other, and applying side sealing between adjacent crotch parts and cutting the sealed portion to complete a single wearing article.

Also, there may be preferably provided a step of attaching elastic members for legs along both leg openings under a stretched state.

Further, a step of attaching an absorber may be preferably provided between the step of forming the shirring in the crotch part and the step of folding the web in two.

In the method of producing a wearing article suitable as trunks for men, no elastic member for legs may be attached along the leg openings.

In this method, in a continuous high-speed production line, the shirring can be easily formed in the substantially widthwise middle portion of the crotch part and the wearing article can be produced at a lower cost.

Also, the shirring can be easily formed by attaching the elastic member for crotch to the substantially widthwise middle portion of the crotch part.

The shirring can be easily formed by forming a wavy portion in the substantially widthwise middle portion of the crotch part.

The shirring can be more easily formed by means of embossing rollers.

Further, the crotch part can be quickly and securely displaced inwardly in the continuous high-speed production line if the crotch part is inwardly displaced by inwardly displacing the web by gripping means.

The gripping means may be formed by gripping claw members or a combination of needle members and pressing members and inward displacing tables may be provided on conveyors or a drum; or gripping means in the form of vacuum holes may be formed in conveyors capable of making inward displacements. Thus, in the continuous high-speed production line, the shirring can be easily and securely formed in the crotch part.

In this method, a wearing article of the bloomers type suitable for women can also be produced if the step of attaching the elastic members for legs along the leg openings is added.

Also, it is also possible to produce a wearing article having an absorber attached to the main body if the step of fixing the absorber to the main body is added. This absorber is preferably exchangeably attached.

The invention claimed is:

1. A trunk-type or bloomers-type wearing article, comprising a main body including a front part and a back part spaced apart along a forward-and-backward direction and a crotch part coupling the front and back parts, the crotch part having opposite widthwise sides spaced apart along a width direction that is transverse to the forward-and-backward direction so that the crotch part defines a selected width, in the width direction wherein:

the main body includes a pair of waist edges opposed to each other along the forward-and-backward direction and a pair of leg edges opposed to each other along the width direction, elastic members secured in a substantially widthwise middle portion of the crotch part of the main body between the widthwise sides of the crotch part so that a width dimension of areas of the crotch part that have the elastic members is narrower than the width of the crotch part and so that the elastic members form a shirring to shorten a space between the front and back parts, the space between the front and back parts is shorter at the widthwise middle portion of the crotch part than at both widthwise sides of the crotch part, the crotch part forming an inverted fork shape upon wearing the trunk-type or bloomers-type wearing article so that the widthwise sides of the crotch part are below the widthwise middle portion of the crotch part and so that the widthwise sides of the crotch part define parts of legs of the trunk-type or bloomers-type wearing article, and a ratio of the length of the crotch part along the forward-and-backward direction to a length between the pair of waist edges is 1:15 to 1:2.

2. A trunk-type or bloomers-type wearing article according to claim 1, wherein the shirring is formed by making folds in the substantially widthwise middle portion of the crotch part of the main body to shorten the substantially widthwise middle portion in a direction coupling the front and back parts and by retaining the wavy shape of the substantially widthwise middle portion.

3. A trunk-type or bloomers-type wearing article according to claim 2, wherein elastic members for legs are attached along the leg edges under a stretched state.

4. A trunk-type or bloomers-type wearing article according to claim 2, wherein an absorbent is attached to the main body.

5. A trunk-type or bloomers-type wearing article according to claim 2, wherein a gore is formed at the crotch part by the shirring when the wearing article is worn.

6. A trunk-type or bloomers-type wearing article according to claim 1, wherein the shirring is formed by the shrinking force of an elastic member attached to the substantially widthwise middle portion of the crotch part of the main body under a stretched state in a direction coupling the front and back parts.

7. A trunk-type or bloomers-type wearing article according to claim 6, wherein elastic members for legs are attached along the leg edges under a stretched state.

8. A trunk-type or bloomers-type wearing article according to claim 7, wherein a gore is formed at the crotch part by the shirring when the wearing article is worn.

9. A trunk-type or bloomers-type wearing article according to claim 7, wherein an absorbent is attached to the main body.

10. A trunk-type or bloomers-type wearing article according to claim 9, wherein a gore is formed at the crotch part by the shirring when the wearing article is worn.

11. A trunk-type or bloomers-type wearing article according to claim 6, wherein an absorbent is attached to the main body.

12. A trunk-type or bloomers-type wearing article according to claim 6, wherein a gore is formed at the crotch part by the shirring when the wearing article is worn.

13. A trunk-type or bloomers-type wearing article according to claim 12, wherein the gore is defined substantially at the widthwise middle portion of the crotch part and extends up toward a wearer.

14. A trunk-type or bloomers-type wearing article according to claim 12, wherein the elastic member in the widthwise middle portion of the crotch part has a widthwise dimension less than widthwise dimensions of the crotch part as measured between the respective leg edges.

15. A trunk-type or bloomers-type wearing article according to claim 1, wherein elastic members for legs are attached along the leg edges under a stretched state.

16. A trunk-type or bloomers-type wearing article according to claim 1, wherein an absorbent is attached to the main body.

17. A trunk-type or bloomers-type wearing article according to claim 1, wherein a gore is formed at the crotch part by the shirring when the wearing article is worn.

18. A trunk-type or bloomers-type wearing article according to claim 1, wherein a distance between the widthwise middle portion of the crotch part and the waist edges is less than a distance between the widthwise sides of the crotch part and the waist edges.

* * * * *